United States Patent [19]
Kitov

[11] Patent Number: 4,915,110
[45] Date of Patent: Apr. 10, 1990

[54] THERAPEUTIC ELECTROSTATIC DEVICE

[75] Inventor: Zeev Kitov, Jerusalem, Israel

[73] Assignee: Theri-Teck, Inc., Annapolis, Md.

[21] Appl. No.: 223,349

[22] Filed: Jul. 25, 1988

Related U.S. Application Data

[63] Continuation-in-part of Ser. No. 84,178, Oct. 12, 1987, abandoned.

[30] Foreign Application Priority Data

Aug. 21, 1986 [IL] Israel .......................................... 79788

[51] Int. Cl.$^4$ ................................................. A61N 1/00
[52] U.S. Cl. .................................. 128/783; 128/419 F; 600/11
[58] Field of Search ................ 128/783, 419 F; 600/9, 600/11, 13, 14, 15

[56]         References Cited
         U.S. PATENT DOCUMENTS

| | | | |
|---|---|---|---|
| 3,890,953 | 6/1975 | Kraus et al. ...................... | 128/419 F |
| 4,157,087 | 6/1979 | Miller et al. ......................... | 128/422 |
| 4,233,965 | 11/1980 | Fairbanks .............................. | 128/1.5 |
| 4,266,532 | 5/1981 | Ryaby et al. ...................... | 128/419 F |
| 4,428,366 | 1/1984 | Findl et al. ............................ | 128/1.5 |
| 4,501,265 | 2/1985 | Pescatore ......................... | 128/419 F |
| 4,537,195 | 8/1985 | McDonnell .......................... | 128/422 |
| 4,556,051 | 12/1985 | Maurer .............................. | 128/419 F |
| 4,574,809 | 3/1986 | Talish et al. ........................... | 600/13 |

Primary Examiner—Francis Jaworski
Assistant Examiner—George Manuel
Attorney, Agent, or Firm—Sandler & Greenblum

[57]         ABSTRACT

There is provided an electrode device for making contact with a living body surface, comprising an electrical current conductive element configured to have a face with a restricted cross-sectional area and including a current insulating material affixed to the face and an electrical terminal means affixed to the element, a current conductive member having a first and a second face, a current insulating material affixed to the first face and an electrical terminal means located on the second face, and means for supporting the element and the member in proximity to each other and with the insulating material facing in the same direction to form a surface for making contact with selected points on the living body surface. An electronic apparatus incorporating the electrode device is also described.

17 Claims, 4 Drawing Sheets

THERAPEUTIC ELECTROSTATIC DEVICE

This application is a continuation-in-part of copending application Ser. No. 084,178 filed Oct. 12, 1987, and now abandoned.

The present invention relates to a device and an apparatus for the stimulation and sedation of nerves and more particularly, to a device and electronic apparatus for effecting electrostatic therapy to selected points of a body, which may include acupuncture points.

Body treatment by acupuncture technique is ancient. The newer developments in this field are based in the classical acupuncture practice of the insertion of needles at the known acupuncture points and the stimulation of the nerves by manually vibrating the needles with the modification that the vibrations are now effected by various more sophisticated means such as, pulsating electric currents. While this method of treatment has been reported as being effective in, e.g., pain relieving, such transcutaneous nerve stimulation methods inherently possess the risks of causing damage to the body due to accidental bending or breakage of a needle tip and other known dangers. There was, therefore, developed a new system of treatment, known as electromagnetic acupuncture, whereby strong magnetic fields are externally applied to body parts, the theory being that these magnetic fields interact with the body's inner electrical field and generate currents. Only when the generated magnetic field reached a certain intensity, results, such as local analgesia, were observed. Thus this method of magnetic and electromagnetic treatments suffers from the disadvantage of the need to use relatively high electrical and/or magnetic energy which is, of course, undesired in all aspects.

It is therefore a broad object of the present invention to ameliorate the disadvantages of the prior art methods of acupuncture therapy and to provide means for effecting stimulation and sedation of nerves of the body by applying an electrostatic field generated by low voltage to selected points of a body.

According to the present invention there is provided an electrode device for making contact with a living body surface, comprising an electrical current conductive element configured to have a face with a restricted cross-sectional area and including a current insulating material affixed to said face and an electrical terminal means affixed to said element, a current conductive member having a first and a second face, a current insulating material affixed to said first face and an electrical terminal means located on said second face, and means for supporting said element and said member in proximity to each other and with said insulating material facing in the same direction to form a surface for making contact with selected points on said living body surface.

The invention further provides an electronic apparatus for effecting electrostatic therapy to selected points on a living body surface, comprising a device having an electrical current conductive element having current insulating material affixed to one of its ends and an electrical terminal means affixed on said element, a current conductive member having a first and a second face, a current insulating material affixed to said first face and an electrical terminal means located on said second face, means for supporting said element and said member in proximity to each other and with said insulating material facing in the same direction to form a surface for making contact with selected points on said living body surface, and electrical circuit means responsible for the application of current to said element and member for generating electrostatic fields about said points, said circuit means including a low power DC source activating a pulse generator, and switch means for selecting the polarity of the interconnection between said DC power source and the terminal means of said element and member.

In a modified aspect of the present invention there is provided an electronic apparatus for effecting electrostatic therapy to selected points on a living body surface, comprising a current carrying coil, said coil having current insulating material affixed onto its surface and electrical terminals, means for supporting said coil in a configuration of at least a segment of an annulus, and electrical circuit means responsible for the application of current to said terminals for generating electrostatic fields at the center of said annulus, said circuit means including a low power DC source activating a pulse generator, and switch means for selecting the polarity of the interconnection between said DC power source and the terminals of said coil.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 12 is a cross-sectional view of the assembly of FIG. 11 with the device 2 ghosted in.

Figure 1:
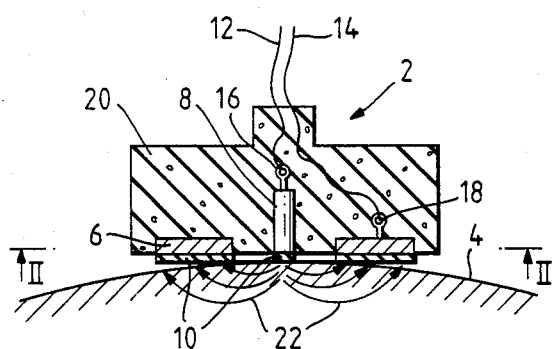
FIG. 1 is a cross-sectional view of a preferred embodiment of a device according to the present invention.

There is shown in FIG. 1 a preferred embodiment of a non-invasive body contacting device 2, for effecting electrostatic therapy to acupuncture points of a body part 4. The device consists of a current conductive annular disk 6 and a centrically located current conductive pin-like element 8. The body facing surfaces of the disk 6 and the element 8 are covered with current insulating material 10. The material 10 should be non-absorbent to moisture, sweat or water, so as to avoid any loss of current insulation capability during use. Electrical wires 12 and 14 are respectively connected to the disk 6 and element 8 by means of terminals 16 and 18, and said wires lead to a low power DC source described hereinafter. The various parts of the device may be encased in an electrically insulating housing 20, which housing as shown in FIG. 1, does not cover the body facing insulating material 10, however, in other embodiments may also constitute the insulating material of the element and disk. The advantages of the above described structure of the device 2, mainly reside in the point surface area of the pin-like element 8 relative to the much larger surrounding surface area of the disk 6, which structure facilitates the application of the device to a specific selected point while spreading the induced electrostatic field 22 about the tip of the element 8 through the treated body part 4 surrounding the selected point as shown.

Since polarization effect, namely, the application to a body of electrodes connected to a source of electrical energy, is proportional to the potential gradient of the tangented component of the field produced by the electrodes, it is usually desired that the gap between the pin-like element 8 and the disk 6 be minimized. Thus with the application of a relatively low potential of about, e.g. 0.5 volt to the wires 12 and 14, there have been observed analgesic effects of the treated body part.

Figure 2:
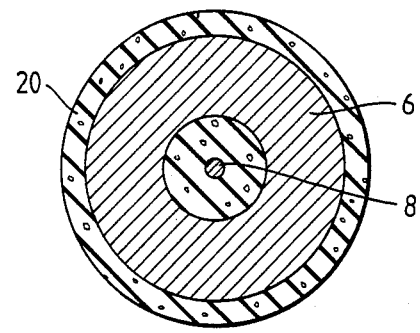
FIG. 2 is a cross-sectional top view across a second embodiment according to the present invention.

In FIG. 2 there is shown a cross-sectional top view of a second embodiment in which instead of the pin-like element 8 there is provided a disc element 9 of a point or very limited surface area similar to the point surface area of the pin-like element 8. Obviously the element 9 is provided with a terminal 16 (not shown) for connection via a wire 12 to a power source.

It should be realised that the disk 6 may be replaced with members of different configurations, e.g., one or more segments of a disk, a plate, a bar or the like.

Figure 3:
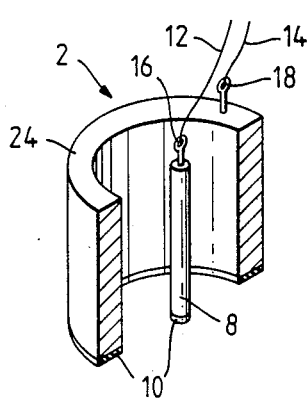
FIG. 3 is a longitudinal cross sectional view of a further embodiment of a device according to the invention.

Another convenient structure of a device 2 is illustrated in FIG. 3, however, for the sake of simplicity there is not shown the housing part encasing the inner parts. Here, the centrically disposed pin-like element 8 is surrounded by a current conductive cylinder 24.

Figure 4:
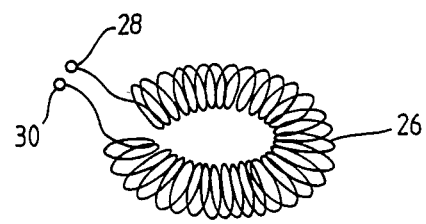
FIG. 4 is a modified device, in a form of an annular coil, in accordance with the present invention.

A modification of the devices 2 illustrated in FIGS. 1 to 3 is shown in FIG. 4. This device consists of a coil 26 in the form of a toroid connectable to a low voltage DC source via terminals 28 and 30. The center of the coil 26 is placed over a selected point on the patient and the electric current flowing in the coil induces a field having a therapeutic effect.

While the device 2 itself is operatable merely by connecting the same to a low voltage DC source, it should be noted that a proper treatment should take into consideration the various stimulation patterns, namely, the direction and strength of the field, the frequency of the impulses including the interval between trains of impulses and of course, the duration of an applied treatment, the intervals between treatments and the time of day the treatment is administered. Since such treatments have to be periodically repeated the present invention provides an apparatus which is programmable to provide a predetermined stimulation pattern suitable to a specific patient who can, thus, administer the treatment to himself under the guidance of a professional.

Figure 5:
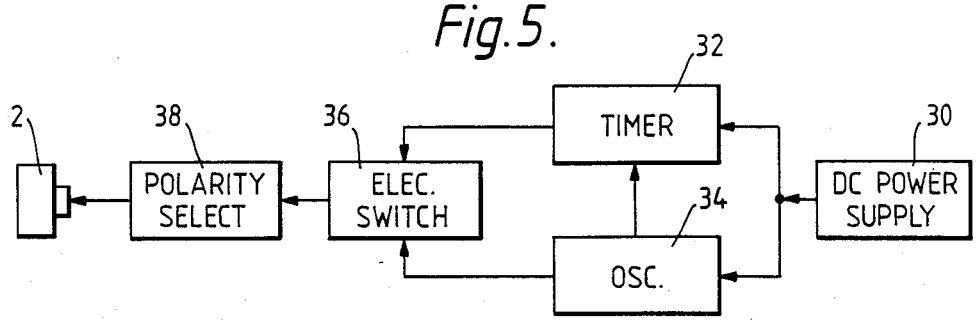
FIG. 5 is a block diagram of a self-contained apparatus for use in accordance with the present invention.
Figure 6:
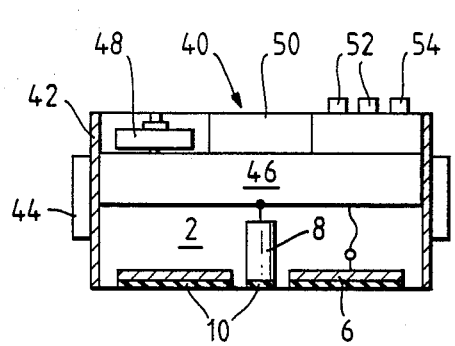
FIG. 6 is a partial cross-sectional view of an electronic unit including the device of FIG. 1.

An example of such an apparatus is illustrated in FIGS. 5 and 6. A DC power supply 30 feeds a programmable timer 32 and an oscillator 34. The timer 32 controls an electronic switch 36 selectively passing impulse signals to a polarity selection switching unit 38, which unit is responsible for the application of the current signals to the device 2 in a selected direction. The direction of the current flow to the element and member of the device governs the direction of the field induced by the current and in turn, the direction of the field, and is significant to this type of treatment. Therefore, when a plurality of devices 2 are to be simultaneously activated, there may be interconnected between each of the devices and the electronic switch 36 a separate polarity selection switching unit to enable the operator to assign to each of the devices the required polarity for treating a designated selected point. Naturally, further sophistication of the apparatus can be obtained by providing a programmer capable of applying to each of the devices placed on individual selected points, a pre-programmed specific stimulation pattern thus achieving a more complete treatment controlled by a single central programmable apparatus.

In order to facilitate the convenient usage of the apparatus, the main functions of which apparatus are illustrated in FIG. 5, the apparatus is advantageously packaged as a compact, small size wristwatch like unit 40, as seen in FIG. 6. The inside of a casing 42, furnished with lugs 44 for facilitating the attachment of straps, is allocated into several compartments. In the bottom side of the casing 42 there is mounted the device 2 of FIG. 1. The intermediate compartment 46 contains the electronic circuits, the functions of which were exemplified in blocks 32, 34 and 36 of FIG. 5. The upper portion of the casing contains a DC power supply in the form of a small battery 48, an optional LCD display 50 and programming switches 52 for entering the desired program of the stimulation pattern as explained hereinbefore. The mode selection switch 54 functions as a polarity selection. The unit 40 may thus be manually applied to any chosen point and held in place for the duration of the treatment or alternatively, may be removably attached to the region of treatment on the body. There are, however, places on the body where it is very difficult to strap on the unit or wear it and where important selected points exist. Also, in cases in which treatments are often or even continuously required, the present invention provides for a convenient way of effecting electrostatic therapy by the incorporation of the device or several devices 2, or even entire units 40 into a body-part shaped covering for example a glove, a stocking or the like, which covering can be worn by the user.

Figure 7:
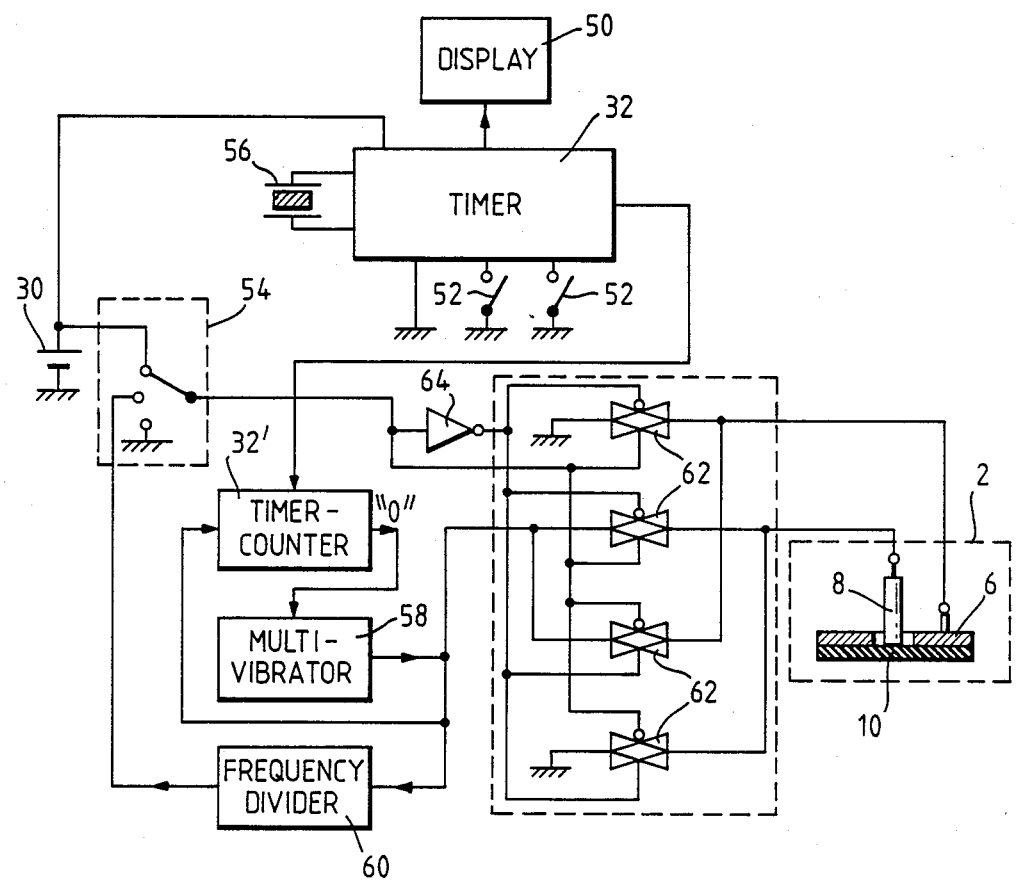
FIG. 7 is a more detailed circuit and block diagram of the apparatus according to the present invention.

An electrical diagram of the device is shown on FIG. 7. A first timer 32 which may consist of a, per-se known, conventional programmable watch timing circuit with an alarm output, is powered by battery 30 and has a quartz crystal frequency stabilizer 56, a number of programming switches 52 and a digital display 50. The timer 32 serves for presetting a desired date and hour of treatment. A second timer 32', has an initiating input connected to an alarm output of the timer 32, while its clock input is connected to an output of an astable multivibrator 58. This connection enables an initiation of the multivibrator activity upon being actuated by an output signal at the predetermined time set by the timer 32.

The second timer 32' acts as programmable countdown counter providing a "0" output. When the logic signal at the output of the timer 32' becomes "0" the astable multivibrator 58 is disabled.

A frequency divider 60 receives input pulses from an output of the astable multivibrator 58 and its output leads to a central terminal of a mode selection switch 54. The divided frequency provided by the divider 60 makes it possible to achieve a periodical switch of polarity, of the output signals applied to the device 2.

A polarity switching unit 38 consists of four analog CMOS switches 62 controlled by a double-rail logic signal applied by the mode switch 54 via an inverter 64. The switch 54 being in one of three possible positions, provides a logic "1", a logic "0", or an intermittent signal to the control lines of the polarity switch 38. Being in the intermittent mode, the polarity switching unit 38 receives on its control lines a signal which is switched over at a rate of about 1-2 times per minute. This rate is established by the frequency divider 60.

The switches 62 are connected to the device 2 so that pulses generated by the astable multivibrator 58 are provided directly to the element 8 and a ground potential to the conductive disk 6, or vice versa.

Figure 8:
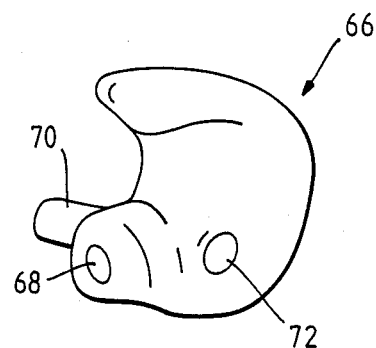
FIG. 8 is a plan view of an auricular assembly incorporating the device or electric unit according to the invention.

In FIG. 8 there is illustrated an auricular assembly 66 comprising a molded ear shaped body attachment having a hearing tunnel 68 and two locations 70 and 72 for holding suitably configured entire units 40 or merely devices 2. operatable from a central control unit which may be located at another place. The devices 2 are strategically oriented to make contact with a selected point which can thus be automatically stimulated at any time of day and night.

Figure 9:
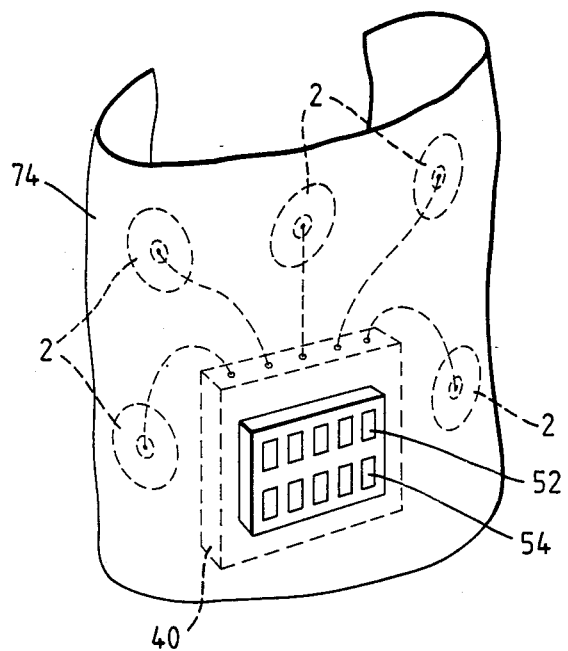
FIG. 9 is a further embodiment of a body portion shaped assembly incorporating the device according to the invention.

Treatment of different disorders may require use of different combinations of acupuncture points. In order to provide a multipurpose device for treatment of different disorders, an apparatus with plurality of devices 2 embedded in or affixed to a body-part shaped covering 74 as shown in FIG. 9, is used. Shown is a unit 40 wired to devices 2 strategically positioned to exactly fit acupuncture points of the covered area of the body, when the covering is worn. Switches 52, 54 are exposed for manual programming of the unit 40. As seen, each device 2 is positioned to face with its insulating material 10, an acupuncture point and connected by wires to output terminals 76 of the unit 40.

Figure 10:
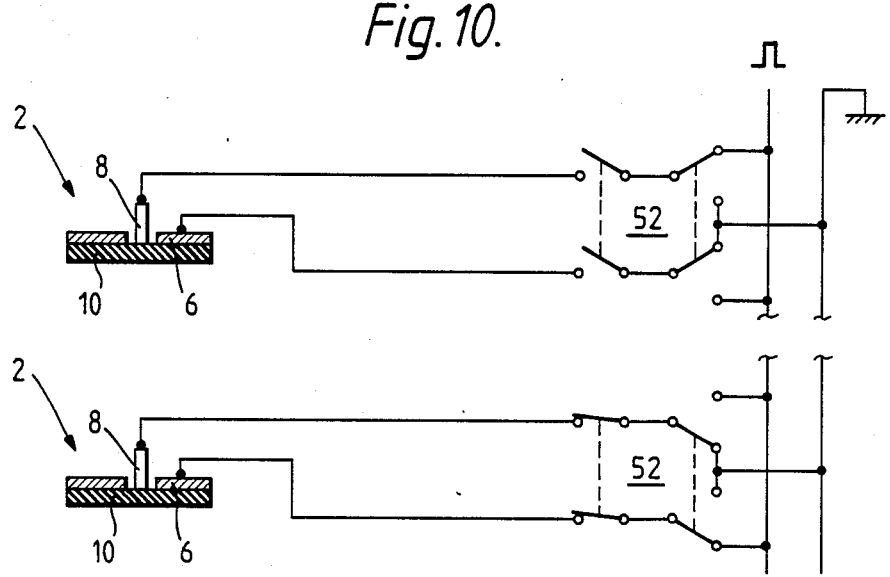
FIG. 10 is a circuit diagram schematically demonstrating the operation of the activating switches.

An electrical diagram of the wiring of the devices 2 is shown in FIG. 10. Switches 52 and 54 on the unit 40 are used for connection/ disconnection of each of the devices 2 and respectively for establishing either a positive or a negative mode i.e., connecting a conductive element 8 of the device 2 to an output pulse line and the conductive disk 6 to the ground line, or vice versa, as described hereinabove.

Figure 11:
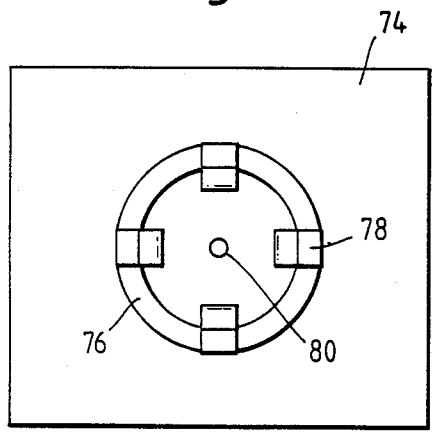
FIG. 11 is a plan view of an assembly for positioning the device according to the invention.
Figure 12:
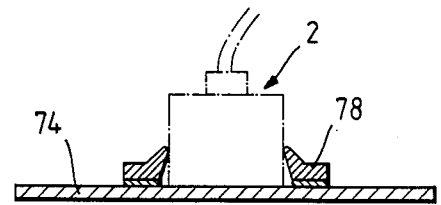

The treatment of selected points of the body, or acupuncture treatment, demands an exact positioning of the centre of the device 2 on the skin to the selected point. The selected points are usually found by commercially available tracers and marked by water soluble ink before the attachment of the device. In order to facilitate the exact positioning of the device on the skin, there is proposed the assembly illustrated in FIGS. 11 and 12. As seen in these figures, a layer 74 of flexible, transparent, electrically isolative material having on one of its sides adhesive material and provided on the other side with rigid a ring 76 attached to the transparent layer 74. The ring 76 has at least two spring-type catches 78. The centre of the ring is marked on the surface of the transparent layer by a point 80. The layer 74 is affixed onto a skin surface in such a way, so that the centre of the ring 76 fits over the designated selected point. The layer 74 is then glued to the skin surface and the device 2 is inserted inside the ring (active side of the device facing the layer) and latched by the catches 78.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An electrode device for making contact with a living body surface, comprising: an electrical current conductive element configured to have a surface with a restricted cross-sectional area and including a current insulating material affixed to said surface and an electrical terminal means affixed to said element, an electrical current conductive member having a first surface and a second surface, a current insulating material affixed to said first surface and an electrical terminal means located on said second surface, and means for supporting said element and said member in proximity to each other with said insulating material forming a surface adapted for body contact with selected points on said living body surface.

2. The device as claimed in claim 1 wherein the surface area of said member is larger than the cross-sectional area of said element.

3. The device as claimed in claim 1 wherein said element is a pin-like element.

4. The device as claimed in claim 1 wherein said element is a disk-like element.

5. The device as claimed in claim 1 wherein said member is a plate.

6. The device as claimed in claim 1 wherein said member is at least a segment of an annular disk and said element is located in its center.

7. The device as claimed in claim 1 wherein said member is in the form of a cylinder and said element is located along its axis.

8. The device as claimed in claim 1 further comprising a housing encasing major portions of said element and said member.

9. The apparatus as claimed in claim 1 further comprising attachment means for removably affixing said electrode device onto a user's body part.

10. The apparatus as claimed in claim 9 wherein said attachment means includes a covering incorporating a plurality of electrode devices, said covering being configured to substantially correspond to the configuration of a living body surface portion when worn by a user, said devices being embedded in said covering at preselected locations, with said surface adapted for body contact facing the inside of said covering.

11. The apparatus as claimed in claim 10 further comprising switch means for selectively connecting each of said devices to a pulse generator in a predetermined polarity.

12. An electronic apparatus for effecting electrostatic therapy to selected points on a living body surface, comprising: a device including an electrical current conductive element having a current insulating material affixed to one of its ends and an electrical terminal means, and a current conductive member having a first surface and a second surface, a current insulating material affixed to said first surface and an electrical terminal means connected to said second surface, means for supporting said element and said member in proximity to each other with said insulating material forming a surface adapted for body contact with selected points on said living body surface, and electrical circuit means for application of current to said element and member for generating electrostatic fields in the region where body contact is made, said circuit means including a low power DC source activating a pulse generator, and switch means for selecting the polarity of the interconnection between said DC power source and the terminal means of said element and member.

13. The apparatus as claimed in claim 12 wherein said circuit means further include a programmable timer for the device at preselected time intervals and for setting the durations of time of each of said activations.

14. An electronic apparatus for effecting electrostatic therapy to selected points on a living body surface, comprising a current carrying coil, said coil having current insulating material affixed onto its surface and having electrical terminals, means for supporting said coil in a configuration of at least a segment of an annulus defining a center, and electrical circuit means connected to said terminals for the application of current to said coils for generating electrostatic fields at the center of said annulus, said circuit means including a low power DC source activating a pulse generator, and switch means for selecting the plurality of the interconnection between said DC power source and the terminals of said coil.

15. The apparatus as claimed in claim 9 further comprising attachment means for removably affixing said device onto a user's body part.

16. The apparatus as claimed in claim 15 wherein said attachment means include a covering incorporating a plurality of said device, said covering being configured to substantially correspond to the configuration of a living body surface portion when worn by a user, and said plurality of said device are embedded in said covering at preselected locations, with said surface for making contact facing the inside of said covering.

17. The apparatus as claimed in claim 16 further comprising switch means accessible from the outside of said covering for selectively connecting each of said devices to a pulse generator in a predetermined polarity.

* * * * *